(12) United States Patent
Lee et al.

(10) Patent No.: US 8,512,722 B2
(45) Date of Patent: Aug. 20, 2013

(54) ANTIMICROBIAL MATERIALS

(75) Inventors: Choon Woo Lee, La Canada, CA (US); Robert H. Grubbs, South Pasadena, CA (US); Mark Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 115 days.

(21) Appl. No.: 12/842,593

(22) Filed: Jul. 23, 2010

(65) Prior Publication Data
US 2011/0059146 A1    Mar. 10, 2011

Related U.S. Application Data

(60) Provisional application No. 61/228,839, filed on Jul. 27, 2009.

(51) Int. Cl.
*A01N 25/10* (2006.01)

(52) U.S. Cl.
USPC ............. 424/404; 424/78.09; 424/78.18; 424/78.37; 424/405; 424/406; 424/407; 424/409; 424/411; 424/412; 428/473.5; 428/474.4

(58) Field of Classification Search
None
See application file for complete search history.

(56) References Cited

U.S. PATENT DOCUMENTS

| | | |
|---|---|---|
| 6,482,402 B1 | 11/2002 | Kurtz et al. |
| 2004/0022759 A1 | 2/2004 | Mandeville et al. |
| 2004/0062744 A1 | 4/2004 | Miyamoto et al. |
| 2008/0152685 A1 | 6/2008 | Blackwell et al. |
| 2008/0226728 A1 | 9/2008 | Domb et al. |
| 2008/0260804 A1 | 10/2008 | Morris et al. |
| 2008/0286225 A1 | 11/2008 | Schonemyr et al. |
| 2009/0226394 A1 | 9/2009 | Champ et al. |

FOREIGN PATENT DOCUMENTS

| | | |
|---|---|---|
| WO | WO 2006/117382 | 11/2006 |
| WO | 2009/115477 A2 | 9/2009 |

OTHER PUBLICATIONS

Beyth et al., Surface antimicrobial activity and biocompatibility of incorporated polyethylenimine nanoparticles, Biomaterials, vol. 29, Issue 31, pp. 4157-4163.
International Search Report for International Patent Application No. PCT/US2010/043074, Apr. 26, 2011, 3 pages in length.
Lin et al., "Insights into bactericidal action of surface-attached poly-(vinyl-*N*-hexylpyridinium) chains", Biotechnology Letters, Jan. 1, 2002, vol. 24, No. 10, 801-805.

*Primary Examiner* — Neil Levy
(74) *Attorney, Agent, or Firm* — Woodcock Washburn, LLP

(57) ABSTRACT

The disclosure provides methods and materials suitable for preparing coating layers on substrates. The coatings comprise quaternary amine groups and therefore impart anti-bacterial properties to the substrate. In one embodiment, for example, there is provided a quaternary amine-containing polymeric coating comprising propylene and ethylene repeat units.

14 Claims, 2 Drawing Sheets

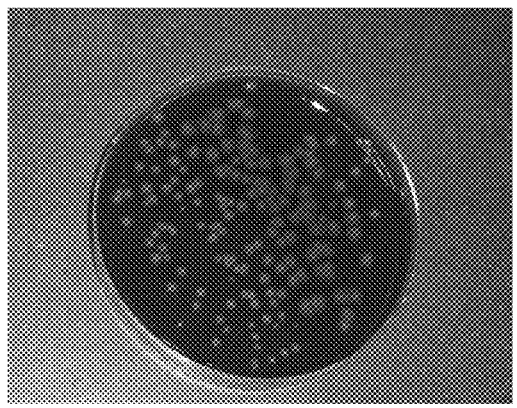 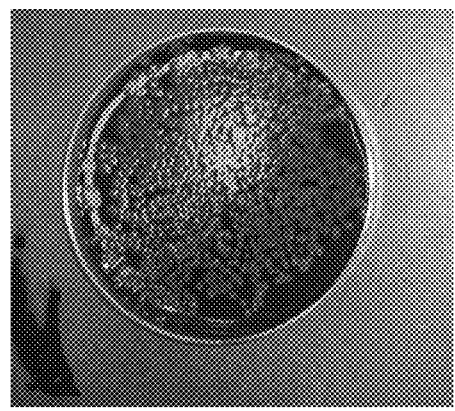
FIG. 2a  FIG. 2b
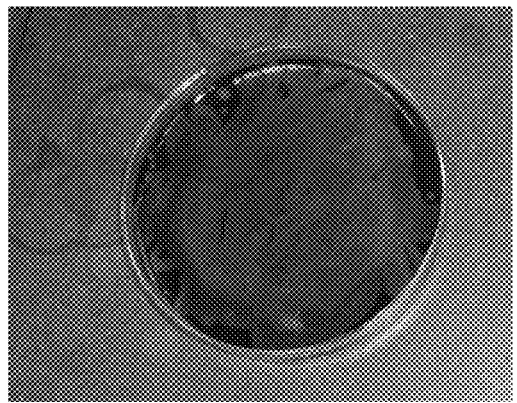
FIG. 2c

ANTIMICROBIAL MATERIALS

CROSS REFERENCE TO RELATED APPLICATIONS

This application claims priority under 35 U.S.C. §119 to U.S. Provisional Application Ser. No. 61/228,839, filed Jul. 27, 2009, the contents of which is incorporated herein by reference in its entirety.

TECHNICAL FIELD

The present invention is directed to materials and methods suitable for providing an object surface with antimicrobial properties. The invention finds utility, for example, in the fields of chemistry and surface coatings.

BACKGROUND

Bacterial infections are common in a variety of circumstances, and are responsible for necessitating a large number of medical interventions each year. Over the past 100 years, numerous antibiotic agents have been developed with varying levels of efficacy. Unfortunately, primarily due to the misuse of antibiotics, antibiotic-resistant strains of bacteria have become more common recently. As antibiotics become less effective against bacterial infections, avoidance of the infections becomes increasingly important and an increasingly preferable approach.

At present, bacteria can populate most surfaces commonly encountered by individuals. For example, the materials used to prepare door knobs, computer keyboards, touch screens, hand rails, and the like do not typically have anti-bacterial properties, and the spread of bacteria within a population is typically limited only by the precautions taken by individuals. For example, proper hygiene (e.g., frequent hand washing) is a highly effective way to avoid bacterial infections of individuals, but requires active participation by the individual and is therefore not always a reliable method. Frequent cleaning and disinfecting of public surfaces and items that are handled by multiple individuals is not always possible and remains a labor intensive method to minimizing the spread of bacteria. Even under nearly ideal conditions, where individuals are taking all practical precautions to avoid the spread and growth of bacteria, certain environments remain prone to bacterial growth. Examples include surfaces that are routinely exposed to aqueous environments for prolonged periods of time. Such surfaces may require thorough cleaning on a regular basis, and where such cleaning is improper, incomplete, or nonexistent bacterial growth may result.

One approach to preventing the spread of bacteria and bacterial infections from exposure to bacterial growth is to provide object surfaces with inherent anti-bacterial activity, such as with a surface coating that imparts such properties. Ideally, such a method would be easily adapted for a variety of object surfaces, would use commonly available and inexpensive materials, would provide long-term anti-bacterial activity with minimal or no toxicity toward animals, and/or would not contribute to the growing incidence of drug-resistant bacteria.

SUMMARY OF THE INVENTION

The present invention is directed to providing methods and materials for providing anti-bacterial object surfaces that satisfy one or more of the abovementioned ideal properties.

In one aspect, there is provided a method for forming an anti-microbial surface coating on a substrate. The method comprises: 1) providing a pre-amine material comprising a plurality of functional groups; 2) reacting the plurality of functional groups with an amine-containing reagent suitable to convert at least a portion of the functional groups to amine groups; and 3) reacting the amine groups from 2) with a quaternary amine conversion reagent suitable to convert at least a portion of the amine groups to quaternary amine groups.

In another aspect, there is provided an anti-microbial coated substrate comprising a substrate and a coating disposed on a surface of the substrate. The coating comprises a polymer that is non-covalently attached to the substrate. The polymer comprises a plurality of quaternary amine groups.

In another aspect, there is provided a coating layer on a surface of a substrate comprising a polymeric material comprising quaternary amine groups covalently attached to the polymeric material. The polymeric material is non-covalently attached to the substrate surface.

Other aspects of the invention will be apparent from the description that follows, including the claims and examples.

BRIEF DESCRIPTION OF THE DRAWINGS

FIG. 2 provides images of *P. Aeruginosas* bacterial cultures that resulted from the antibacterial screening studies described in the Examples provided herein.

DETAILED DESCRIPTION OF THE DISCLOSURE

Figure 1A:
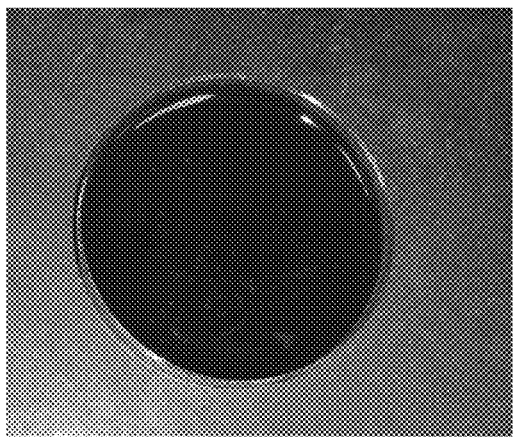
FIG. 1 provides images of *S. Aureus* bacterial cultures that resulted from the antibacterial screening studies described in the Examples provided herein.

Before describing the present invention in detail, it is to be understood that unless otherwise indicated, this invention is not limited to any particular material or method of synthesis described herein, as such may vary. For example, where a polypropylene substrate is identified, it is not intended that the invention is limited to polypropylene substrates unless otherwise stated. It is also to be understood that the terminology used herein is for the purpose of describing particular embodiments only, and is not intended to be limiting. The definitions provided herein are not meant to be mutually exclusive. For example, it will be appreciated that some chemical groups may fit into more than one definition.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. "Substituted alkyl" includes, for example, instances where two hydrogen atoms from the same carbon are replaced, such as in a carbonyl group. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

If not otherwise indicated, the term "unsaturated alkyl" includes alkenyl and alkynyl, as well as combinations thereof.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings (such as 1 to 3 rings) that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to an aryl substituent, in which at least one carbon atom is replaced with a heteroatom, as will be described in further detail infra. If not otherwise indicated, the term "aryl" includes unsubstituted, substituted, and/or heteroatom-containing aryl substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "olefinic group" intends a mono-unsaturated or di-unsaturated hydrocarbon group of 2 to 12 carbon atoms. Preferred olefinic groups within this class are sometimes herein designated as "lower olefinic groups," intending a hydrocarbon moiety of 2 to 6 carbon atoms containing a single terminal double bond. The latter moieties may also be termed "lower alkenyl."

The term "alkylene" as used herein refers to a difunctional saturated branched or unbranched hydrocarbon chain containing from 1 to 24 carbon atoms. "Lower alkylene" refers to alkylene linkages containing from 1 to 6 carbon atoms, and includes, for example, methylene (—$CH_2$—), ethylene (—$CH_2CH_2$—), propylene (—$CH_2CH_2CH_2$—), 2-methyl-propylene (—$CH_2$—$CH(CH_3)$—$CH_2$—), hexylene (—$(CH_2)_6$—) and the like.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including unsubstituted, substituted, heteroatom-containing, and substituted heteroatom-containing hydrocarbyl moieties.

"Halo" or "halogen" refers to fluoro, chloro, bromo or iodo, and usually relates to halo substitution for a hydrogen atom in an organic compound. Of the halos, chloro and fluoro are generally preferred.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N═N$^+$═N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR═NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR═N(alkyl), where R=hydrogen, alkyl, aryl, alkaryl, etc.), arylimino (—CR═N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

The invention provides substrates coated on at least one surface with a material that comprises quaternary amine groups. The quaternary amines present in the surface coatings impart anti-bacterial properties to the substrate. The surface coatings are not covalently bonded to the substrate surface, but nevertheless form stable coatings that exhibits minimal or no leaching, dissolution, and/or degradation when exposed to an aqueous environment. Accordingly, the coatings are generally safe for use in biological applications such as coatings on contact lens storage cases. The coatings are also stable in dry environments, and may be used to prevent bacterial growth in a variety of applications as described herein. In some embodiments, the surface coatings are conformal such that they coat the entire substrate surface (i.e., there are no gaps of exposed substrate that could support bacterial growth). In some embodiments, the coatings uniformly cover the substrate surface (e.g., the coating thickness may vary by less than 25%, or by less than 15%, or by less than 10% from the average over the area of the surface covered). Generally, the coatings bond to the substrate surface via one or more of Van der Waals forces, ionic bonding, and hydrogen bonding.

Methods

Methods for preparing the coatings of the invention will vary according to factors such as the type and topography of the surface to be coated, the specific materials used in the coating, the intended use of the coated object, etc. In addition to the procedures described herein (including in the Examples set forth below), the skilled artisan may wish to make reference to the pertinent literature.

In one embodiment, the coatings of the invention are prepared according to the following procedure which is referred to herein as the "primary process." A substrate (i.e., an object to be coated) is provided, and a surface of the substrate to be coated is selected. The selected surface is coated with a first layer of material—the first coating is referred to herein as a pre-amine layer, and the material is referred to herein as a pre-amine material. The pre-amine material comprises functional groups, and the pre-amine layer is subsequently converted (e.g., by reaction of the functional groups with an amine-containing material or by conversion of the functional groups to amine groups) to an amine layer—the material forming the amine layer is referred to herein as an amine-containing material. The amine groups in the amine layer are subsequently converted to quaternary amines to provide a substrate coated with quaternary amines groups.

In another embodiment, the coatings of the invention are prepared according to the following procedure which is referred to herein as the "first modified process." A substrate is provided, and a surface of the substrate to be coated is selected. Separately, an amine-containing material is prepared. The selected substrate surface is coated with the amine-containing material. The amine groups of the amine-containing material are subsequently converted to quaternary amine groups to provide a substrate coated with quaternary amines groups.

In another embodiment, the coatings of the invention are prepared according to the following procedure which is referred to herein as the "second modified process." A substrate is provided, and a surface of the substrate to be coated is selected. Separately, an amine-containing material is provided. The amine groups on the amine-containing material are converted to quaternary amine groups to provide a quaternary amine-containing material (in solution or as a solid). The quaternary amine-containing material is coated onto the selected substrate surface to provide a substrate coated with quaternary amines groups.

Variations of the methods just described are within the scope of the invention, and it will be appreciated that these methods may further comprise additional steps not identified as necessary or desired. For example, a washing step to remove amine-containing material that is not strongly adhered to the substrate surface may be desirable prior to conversion to quaternized amine groups. For each of the above-described methods, the result is a substrate having a coating, wherein the coating comprises quaternary amine groups. The quaternary amine groups are covalently incorporated into the coating. Also, for each of the above-described methods, the first material to be applied to the substrate surface (i.e., the pre-amine material in the primary process, the amine-containing material in the first modified process, and the quaternary amine-containing material in the second modified process) bonds non-covalently to the surface. Such bonding may be via hydrogen bonding, Van der Waals forces, ionic bonding, or any combination thereof. Also, in each of the above-described methods, the final coating materials are substantially water insoluble.

Materials

The invention provides coatings disposed upon substrates. The substrate supports the coatings of the invention, and also provides structural functionality to carry out the applications described herein (e.g., storage, structural support, etc.). The substrate may have a variety of shapes and properties, and may be made from a variety of materials as described in more detail below.

In some embodiments, the substrate is designed to perform a biological function, such as a providing structural support, or functioning as a replacement component for a biological organism, or assisting a medical procedure. In some embodiments, the substrate is designed to provide storage, such as storage of biological samples, objects having a biological function, tools and other materials used in medical procedures, and the like. Examples of substrates suitable for the invention include stents, catheters, and the like.

The shape and topography of the substrate and substrate surface to be coated will be selected according to the intended use. For example, storage containers may include lids that are also intended to be coated with the coatings of the invention.

In some embodiments, the substrate comprises a polymeric material. For example, some preferred polymer materials for the substrate include polyalkylenes such as polyethylene, polypropylene, and polybutylene, vinyl polymers such as polystyrene, poly(vinyl chloride), poly(methacrylate), poly(methylmethacrylate), and poly(isobutylene), polyesters such as poly(ethylene terephthalate), other addition polymers such as polyurethane, and copolymers of the above (e.g., copolymers having alkylene and/or vinyl repeat units). Siloxane (i.e., silicone) polymers are also a preferred substrate material, including polydimethylsiloxane polymers and the like. Natural latex rubber polymers are also a preferred substrate material. Derivatives of any of the foregoing polymers and copolymers are also within the scope of the invention.

In other embodiments, the substrate comprises a metal or alloy. For example, stainless steel commonly used in surgical instruments is a suitable substrate for the coatings of the invention. Other metals such as those commonly used in surgical implants, storage containers, watercrafts hulls, etc. are also suitable as substrates. Examples of specific metals include steels (e.g., carbon steel, alloy steel such as stainless steel, etc.) and alloys containing nickel, titanium, copper, tin, chromium, molybdenum, etc.

In one embodiment (referred to above as the primary process), the substrate is first coated with a pre-amine material. The pre-amine material is a material that comprises functional groups capable of being converted to amine groups. The pre-amine material is (typically although not necessarily) a polymeric material. For example, the pre-amine material may be a chlorinated polymer such as a chlorinated polyalkylene (e.g., chlorinated polypropylene, chlorinated polybutylene, etc.) or a chlorinated vinyl polymer (e.g., chlorinated polystyrene, chlorinated poly(alpha-methylstyrene), chlorinated poly(isobutylene), etc.). Functional groups other than chloro groups are also within the scope of the invention. Examples include bromo or iodo groups, hydroxyl groups, etc. The pre-amine material can range in molecular weights from 1,000 D to 1,000,000 D or more, and is preferably soluble in organic solvents such as toluene or the like. The pre-amine material is deposited onto the substrate surface using any appropriate method of deposition, and the resulting layer is referred to herein as a "pre-amine layer."

Once the pre-amine layer is deposited, the functional groups on the pre-amine material are converted to amine groups. Conversion is generally accomplished by reacting the functional groups with a reagent effective to convert the functional groups to amine groups. For example, in some embodiments, the functional groups are halide groups and are reacted with an amine-containing reagent under conditions effective to convert the halide groups to amine groups. The amine-containing reagent may be, in some embodiments, a polymeric material comprising amine groups in the repeat units of the polymer (either in the polymer backbone, or attached as pendant groups, or a mixture of both). For example, the amine-containing reagent may be a polymer comprising a mixture of primary amines, secondary amines, and tertiary amines. One preferred such material is branched poly(ethyleneimine) (PEI). Another material suitable for the coatings of the invention is linear PEI, which comprises secondary amines. Generally herein, reference to "PEI" is meant to include both linear and branched varieties. PEI may be prepared specifically for the uses described herein, or may be purchased commercially. PEI is generally prepared from ethyleneimine, and may be described as having ethylene amine repeat units. PEI suitable for the coatings of the invention may be linear or branched PEI. Other suitable amine-containing reagents include secondary amines such as dihexyl amine and the like. Other suitable amine-containing reagents include tertiary amines such as poly(vinyl pyridine) and the like. Polymeric and oligomeric amine-containing reagents will typically, although not necessarily, have a molecular weight in the range of about 350 D to about 1,000,000 D, or above about 400 D. Once the pre-amine layer is converted (i.e., amine groups are formed), the coating material is referred to herein as an "amine-containing coating material" (or "amine-containing material"), and the coating is referred to as an "amine layer." It will be appreciated that the composition of the amine-containing coating material will, in some embodiments, be a combination of the materials used in preparation (i.e., the pre-amine material and the amine-containing reagent). The amine-containing coating material may be a crosslinked material, or may be a non-crosslinked material having a molecular weight in the range of about 1,500 D to about 2,000,000 D or greater.

Once the amine layer is formed, the amine groups are converted to quaternary amine groups. Conversion is generally accomplished using an electrophilic alkylating reagent such as an alkyl halide. Any suitable alkyl halide can be used, such as RX where X is halo (Br, Cl, or I) and R is alkyl (Me, Et, n-Pr, i-Pr, n-Bu, i-Bu, t-Bu etc.). Larger alkyl halides and substituted alkyl halides may also be used. Other electrophilic reagents, such as electron-withdrawing aryl halides, may also be used. In embodiments where the amine-containing reagent is a tertiary amine (such as poly(vinyl pyridine)), in some embodiments the reaction product of the amine-containing reagent and the pre-amine material comprises quaternary amine groups. In such embodiments, it is not necessary to react the coating further to form quaternary amine groups (although further conversion to increase the yield of quaternary amine groups may be carried out if desired).

In another embodiment (referred to above as the first modified process), the substrate is as described above for the primary process. An amine-containing material is prepared and coated directly onto the substrate. Thus, in some embodiments, the first modified process comprises converting functional groups to amine groups prior to forming any coatings on the substrate. For example, an amine-containing polymeric material may be prepared by reacting, in solution, chlorinated polypropylene with PEI. The resulting amine-containing material is then coated onto the substrate using any appropriate method (e.g., solution casting or the like). Once the amine-containing layer is thus prepared, the amine groups are converted to quaternary amine groups as described above for the primary process. The materials described above for the primary process may also be used in the first modified process.

In another embodiment (referred to above as the second modified process), the substrate is as described above for the primary process. An amine-containing material is prepared as described for the first modified process (i.e., in solution or otherwise separate from the substrate). The amine-containing material is converted to a quaternary amine-containing material and is then coated onto the substrate. The materials suitable for preparing the quaternary amine-containing material are as described above for the primary process. The materials described above for the primary process may also be used in the second modified process.

The coatings of the invention may further be described as comprising quaternary amine groups covalently attached to a support layer. The support layer is non-covalently attached to the substrate and comprises, for example, the reaction product of the pre-amine material and the amine-containing reagent. As described supra, the pre-amine material and amine-containing reagent may be reacted after deposition of the pre-amine material on the substrate (i.e., the primary process), or may be reacted prior to deposition onto the substrate (i.e., the first and second modified processes). Thus, the support layer comprises a material that may be formed stepwise on the substrate surface (i.e., the primary process), may be formed and then deposited onto the substrate surface (i.e., the first modified process), or may be formed and modified to contain quaternary amines prior to being deposited on the substrate surface (i.e., the second modified process).

The support material is prepared from the pre-amine material which is typically, although not necessarily, a polymeric material. Suitable support materials therefore include polyalkylenes such as polyethylene, polypropylene, and polybutylene, vinyl polymers such as polystyrene, poly(vinyl chloride), poly(methacrylate), and poly(methylmethacrylate), addition polymers such as polyurethanes, polycarbonates, and polyesters, and copolymers thereof (e.g., copolymers having alkylene or vinyl repeat units, or other copolymers such as poly(ethylene terephthalate)). Other materials as described supra are also suitable. Combinations of such polymers are also suitable. In some embodiments, for example, the support material is a polymeric material that comprises repeat units selected from ethylene, substituted ethylenes (e.g., ethylene amine, ethylene oxide, etc.), propylene, butylene, cyclopentane, styrene, vinyl pyridine, methacrylate, methylmethacrylate, butadiene, carbamate, carbonate, terephthalic acid, derivatives thereof, and combinations thereof.

The coatings of the invention comprise quaternary amine groups that are covalently attached to the support material. For example, where the support material is a polymeric material, the quaternary amine groups may be attached to side-groups of the base polymer (or may themselves form side-groups of the polymer), or may be directly incorporated into the polymer backbone. Thus at least one of the groups attached to the nitrogen atoms of the quaternary amine groups is the support material (i.e., in embodiments where the quaternary amine group is, or is attached to, a polymer side-group), and in some embodiments two of the groups attached to the nitrogen atoms of the quaternary amine groups are the support material (i.e., in embodiments where the quaternary amine group is directly incorporated into the polymer backbone of the support material). The remaining two or three groups attached to the nitrogen atoms of the quaternary amine groups may be selected from alkyl (e.g., methyl, ethyl, propyl, etc., including branched, substituted, and cyclic alkyl groups), aryl (e.g., phenyl, substituted phenyl, etc.), alkaryl, and aralkyl (e.g., benzyl, etc.) groups.

In preferred embodiments, the coatings of the invention are highly water insoluble. Accordingly, the coatings of the invention do not allow "leaching" into aqueous environments—i.e., upon exposure to an aqueous environment, substantially none of the material present in the coatings of the invention are dissolved. For example, in some embodiments, less than 25%, or less than 20%, or less than 15%, or less than 10%, or less than 5%, or less than 3%, or less than 1%, or less than 0.1% by weight of the coatings of the invention are leached into an aqueous environment (at room temperature) over a period of 1 hour, or 10 hours, or 15 hours, or 24 hours, or 3 days, or 1 week, or 1 month, or 1 year.

In some embodiments, the coatings of the invention are stable to common processing conditions for the devices and substrates described herein. For example, the coatings are stable toward sterilization using heat, chemical sterilizers (e.g., ethylene oxide), and/or steam.

As described in more detail supra, the support material may be prepared in a number of ways. It will be appreciated that the method selected for preparation of the support material may have a bearing on the final composition and/or the composition of the coating material at any stage in the preparation process. The support material may, in some embodiments, further comprise additional functional or non-functional (i.e., inert) components such as diluents, colorants, anti-oxidants, etc.

In some embodiments, the coatings of the invention cover all external surfaces of the substrate. In some embodiments, the coatings cover only a portion of the external surfaces of the substrate, such as one surface, or a plurality of surfaces. The coatings may be any suitable thickness. A suitable thickness is typically one that allows the coating to fully cover the underlying substrate surface, such that few or no pinholes or bare spots remain. For example, suitable thicknesses include those with the range of about 10 nm to about 0.1 mm, or about 100 nm to about 0.1 mm, or about 1000 nm to about 0.1 mm. For example, suitable thicknesses may be less than about 0.1 mm, or less than about 10 μm, or less than about 1 μm, or greater than about 100 nm, or greater than about 1000 nm, or greater than about 10 μm.

In some embodiments, a coating of the invention is prepared from the same material as the substrate. For example, in some embodiments, the substrate is polypropylene, and the support layer also comprises polypropylene (modified as described herein to contain quaternary amine groups). In some embodiments, the pre-amine material and the substrate comprise the same type of material, but the amine-containing reagent comprises a different material. For example, both the substrate and the pre-amine material comprise polypropylene (in the case of the pre-amine material, a modified polypropylene such as chlorinated polypropylene), and the amine-containing reagent is polyethyleneimine. In some embodiments, the pre-amine material and the amine-containing reagent are both polymers, but comprise different repeat units. In other embodiments, the pre-amine material and the amine-containing reagent are both polymers, and comprise the same repeat units.

In some embodiments, the quaternary amines present in the coatings of the invention comprise the structure of formula (I)

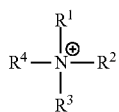

(I)

wherein $R^1$, $R^2$, $R^3$, and $R^4$ are independently selected from hydrocarbyl, substituted hydrocarbyl, heteroatom-containing hydrocarbyl, and substituted heteroatom-containing hydrocarbyl. In some embodiments, $R^1$, $R^2$, $R^3$, and $R^4$ are independently selected from alkyl, alkenyl, alkynyl, aryl, aralkyl, and alkaryl, any of which may contain one or more (e.g., 2, 3, 4, etc.) substituents and one or more (e.g., 2, 3, 4, etc.) heteroatoms. In some embodiments, one of $R^1$, $R^2$, $R^3$, and $R^4$ is a sidechain (comprising, e.g., a linking group selected from alkylene and arylene) that is connected to the backbone of a larger polymer. In some embodiments, the nitrogen atom is part of the backbone of a polymer, such that two (in the case of linear polymers) or three (in the case of branched polymers) of $R^1$, $R^2$, $R^3$, and $R^4$ represent backbone portions of the polymer. In some embodiments one of more of $R^1$, $R^2$, $R^3$, and $R^4$ is selected from $C_1$-$C_{12}$ alkyl, such as methyl, ethyl, propyl, and the like. In some embodiments three of $R^1$, $R^2$, $R^3$, and $R^4$ comprise polymer backbone groups such that the nitrogen atom is a branch point in the polymer material that forms the coating. In such embodiments, the polymer may be branched, highly branched, or cross-linked.

In some embodiments, the coatings of the invention comprise quaternary amines having the structure of formula (I), wherein two or three of $R^1$, $R^2$, $R^3$, and $R^4$ comprise polymeric moieties and the remaining one or two of $R^1$, $R^2$, $R^3$, and $R^4$ are selected from $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, any of which may be substituted and/or heteroatom-containing. In some embodiments, the coatings of the invention comprise quaternary amines having the structure of formula (I), wherein at least one of $R^1$, $R^2$, $R^3$, and $R^4$ comprises a methyl, ethyl, propyl, or butyl group.

In some embodiments, the coatings of the invention are polymers comprising quaternary amine groups having structures selected from (a)-(c)

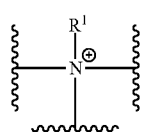

(a)

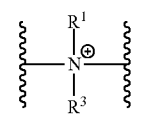

(b)

-continued

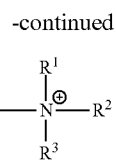

(c)

wherein $R^1$, $R^2$, and $R^3$ are as described above and the wavy lines represent polymeric moieties. Any combination of structures (a)-(c) may be present in the polymeric materials of the invention. For example, in some embodiments, the materials contain only structure (a), whereas in some embodiments the materials contain a combination of structures (a), (b), and (c).

In some embodiments, the coatings of the invention prior to quaternization comprise polymers having the structure of formula (II)

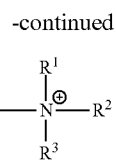

(II)

wherein x and y are non-negative integers (including zero). Subsequent to quaternization of such materials, all or a portion of the nitrogen atoms in the polymer structure are converted to, cationic moieties such as in the structure of formula (IIa)

(IIa)

Accordingly, in some embodiments, the coatings of the invention comprise branched or cross-linked polymers that comprise quaternary amine groups as part of the backbone polymer structure (i.e., "non-terminal" quaternary amines groups). In some embodiments, the coatings of the invention comprise branched or cross-linked polymers that comprise quaternary amine groups as sidegroups (i.e., "terminal" quaternary amine groups) to the polymer structure. In some embodiments, the coatings of the invention comprise branched or cross-linked polymers that comprise both terminal and non-terminal quaternary amine groups.

In some embodiments, the coatings of the invention comprise polymers that contain, on average, one quaternary amine for each repeat unit of the polymer. In some embodiments, the coatings of the invention comprise polymers that contain, on average, more than one quaternary amine for each repeat unit of the polymer in the coating. Compounds having the structure of formula (IIa) are examples of the latter embodiment, since some of the repeat units in the polymer contain two quaternary amine groups. Thus, in some embodiments, the coatings of the invention comprise polymers that comprise a repeat unit having more than one (e.g., two) quaternary amine group.

In some embodiments, the coatings of the invention are prepared from non-peptidic polymeric materials. That is, the materials that form the coatings are synthetic organic polymers and are neither synthetic nor natural polypeptides. That is, in some embodiments, the coatings of the invention are formed from polymers that are other than polyamino acids.

In preferred embodiments, the coatings of the invention have anti-bacterial properties that are inherent in the coatings—i.e., the coatings do not contain antibacterial compounds "dissolved" therein and prone to leaching out of the coatings. For example, the antibacterial coatings of the invention do not contain silver ions dissolved therein. Furthermore, as described supra, the coatings of the invention are not covalently bonded to the substrate surface.

Uses

The coating materials of the invention are suitable for a variety of uses and applications. In some embodiments, the coating materials of the invention are suitable for medical uses such as for coating biomedical devices, medical tools, objects intended to contact a biological organism, and any storage units for storage of such items. For example, the coating materials of the invention are suitable for coating the surfaces of storage containers intended for storage of items such as biologics (e.g., biomedical devices, biologic medications, etc.), corrective eyewear, dental appliances and other dental devices, catheters, stents, pharmaceuticals, medical instruments, and the like. The coating materials of the invention are also suitable in non-medical applications, such as in the food service industry. For example, the coating materials of the invention are suitable for coating the surfaces of storage containers intended for storage of items such as cooking utensils, cleaning solutions, rinse solutions, certain food items, and the like. The coatings of the invention may also be used in the farming and livestock industry, such as to prevent the spread of bacteria in food-processing facilities.

In some embodiments, the coatings of the invention are suitable for preventing bacterial infections and the spread of bacteria in a hospital environment. In such embodiments, the coatings may be applied to various surfaces that commonly support bacterial growth (and therefore exacerbate the spread of bacterial infections), and/or may be applied to medical instruments and other items used in medicine (e.g., catheters, stents, surgical tools, stethoscopes, orthopedic screws, etc).

In some embodiment, the coatings of the invention are suitable for preparing polypropylene contact lens storage cases that will prevent bacterial contamination of lenses. In such embodiment, the quaternized amine coating forms an anti-bacterial coating on at least the inside surface of the storage case. Even with repeated use and minimal cleaning (i.e., simple rinsing with water), the antibacterial properties of the quaternized amine coatings prevent bacterial growth on the surface(s) of the case. Prevention of such growth therefore also prevents bacterial growth when contact lens storage solution and contact lenses are added to the case, which prevents the transfer of bacteria into the eyes of the contact lens wearer. Preferred contact lens cases are prepared from polypropylene. Where polypropylene is used as the substrate, a preferred support layer comprises polypropylene (and may further comprise, for example, polyethylene units, additives, etc.)

Contact lens cases coated with the quaternized amine coatings of the invention may be prepared as single-use storage containers or as multiple-use containers. The containers may be intended for short term storage (e.g., minutes or hours), medium term storage (e.g., overnight or several days) and/or for long terms storage (e.g., weeks or months or longer).

In some embodiments, the coatings of the invention are used to prepare anti-bacterial coatings on contact lenses. Daily-wear, single use, and extended wear contacts (including both hard and soft varieties) may be coated with the coatings of the invention. Accordingly, in one embodiment, the invention includes a contact lens comprising an anti-bacterial coating, wherein the antibacterial coating comprises quaternary amines as disclosed herein.

In another embodiment, the coating of the invention may be used to coat at least one surface of a catheter and/or of a case for storing a catheter. Suitable catheters include urinary catheters, venous catheters, umbilical lines, balloon catheters, and the like.

In another embodiment, the coatings of the invention may be used to coat metals used, for example, in surgical instruments. Surgical tools having a coating according to the invention are less susceptible to supporting and spreading bacterial infections during surgical procedures.

In some embodiments, the coatings of the invention are applied to objects as part of the manufacturing process. That is, the coatings are applied prior to leaving the manufacturing facility. In some embodiments, the coatings are applied (or re-applied) to a re-usable object in a re-sterilization process, which in some embodiments is carried out prior to final sterilization (e.g., using steam or ethylene oxide).

In some embodiments, the coatings of the invention have anti-bacterial properties that suppress (either completely or partially) the growth of a variety of types of bacterial. In some embodiments, the coatings of the invention are biocidal towards a variety of types of bacterial. In some embodiments, the coatings kill and/or suppress the growth of both Gram-positive and Gram-negative bacteria, as well as drug-resistant bacteria. The coatings kill and/or suppress the growth of bacteria selected from the genera *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella, Burkholderia, Acinetobacter, Enterococcus,* and *Francisella*. For example, in some embodiments, the coatings kill and/or suppress the growth of *Pseudomonas aeruginosa, Pseudomonas aeruginosa,* coagulase-negative Staphylococci, *Enterococcus faecalis, Streptococcus viridans, Escherichia coli, Proteus mirabilis,* and/or *Staphylococcus aureus* (including methicillin-resistant *Staphylococcus aureus* (MRSA) and methicillin-susceptible *Staphylococcus aureus* (MSSA)). In some embodiments, the coatings of the invention are effective against bacteria that have infected and bred within protozoa, such as MRSA (methicillin-resistant *Staphylococcus aureus*) bred within acanthameoba. In some embodiments, the coatings of the invention have anti-fungal properties. In some embodiments, the coatings of the invention have anti-protozoan properties (e.g. against acanthameoba).

In some embodiments, the coatings of the invention are disposed on a substrate and are effective to inhibit the growth of bacteria on the substrate. For example, upon exposure to an aqueous medium comprising bacteria, a substrate comprising a coating of the invention will exhibit 70% less, or 80% less, or 90% less, or 95% less, or 98% less, or 99% less, or 99.9% less, or 99.99% less bacterial growth on the substrate over a predetermined period of time (e.g., 1 hour, 10 hours, 24 hours, 48 hours, 72 hours, etc.) compared with a similar substrate lacking such a coating.

In some embodiments, the coatings of the invention are effective to reduce a population of bacteria in a solution contacting the coatings. For example, upon exposure to a solution containing a population of bacteria, a substrate comprising a coating of the invention will reduce the bacterial population in the solution by at least 50%, or at least 60%, or at least 70%, or at least 80%, or at least 90%, or at least 95%, or at least 98%, or at least 99%, or at least 99.9% over a predetermined period of time (e.g., 1 hour, 10 hours, 24 hours, 48 hours, 72 hours, etc.) compared with a similar substrate lacking such a coating.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1

Preparation of Coated Polypropylene

Scheme 1: The primary process for the preparation of antimicrobial polypropylene

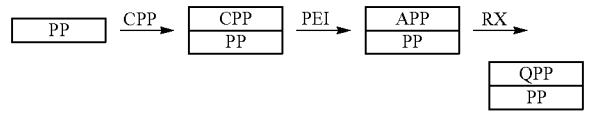

Description of sample preparation. A sample material was prepared according to Scheme 1. Thus, chlorinated polypropylene (CPP; ~26% Chlorine content, Mw~100,000, purchased from Aldrich) was dissolved in toluene at ~100° C. (5 wt % solution). Polypropylene sheet (PP; thickness of 1/16", purchased from MSC Industrial Supply) was sliced into small pieces (1×1 cm), followed by washing with methanol and deionized water to remove impurities on the surface. The surface of polypropylene was carefully coated with 5 wt % CPP solution and dried overnight at ambient temperature under air. The resulting CPP/PP piece was placed into vial, followed by adding 1 mL per piece of 1 wt % polyethyleneimine solution (PEI; Mw~423, purchased from Aldrich and dissolved in acetone or acetonitrile). The mixture was stirred overnight at ~60° C., then the piece was taken out from vial and rinsed with acetone and deionized water. This aminated PP piece (APP/PP) was immersed in a mixture of ethyl bromide (6 wt % solution in acetone or acetonitrile) and triethylamine (0.1 mL per piece). After reaction at ~40° C. for 24 h, the piece was washed with deionized water and acetone. The density of quaternary ammonium groups on the surface was measured by a colorimetric method based on fluorescent complexation and UV-Vis spectroscopy.

Table 1 provides physical characteristics and preparatory methods for the samples prepared.

TABLE 1

Selected data for prepared samples.

| Well # | Sample # | PEI (Mw) | Amination (h) | RX | Base |
|---|---|---|---|---|---|
| 1 | 1 | 423 | 84 | EtBr | |
| 2 | 2 | 423 | 84 | EtBr | Et$_3$N |
| 3 | 5 | 423 | 17 | EtBr | |
| 4 | 6 | 423 | 17 | EtBr | Et$_3$N |
| 5[a] | 7 | 423 | 17 | C10-I | |
| 6[a] | 8 | 423 | 17 | C10-I | Et$_3$N |
| 7[b] | 9 | 423 | 84 | C10-I/EtBr | Et$_3$N |
| 8[c] | 10 | 10000 | 6 | EtBr | Et$_3$N |
| 9[c] | 11 | 10000 | 6 | C10-I | Et$_3$N |
| 10 | PP | — | — | | |
| 11 | CPP/PP | — | — | | |
| 12 | APP/PP | 423 | 17 | | |

[a]C$_{10}$-I is iododecane.
[b]Quaternary ammonium polypropylene/PP prepared with iododecane was resubjected to the mixture of EtBr and Triethylamine.
[c]Branched polyethyleneimine (Mw~10,000) was used.

Example 2

Description for the modified antimicrobial polypropylene coating process. Scheme 2 shows a modified method for antimicrobial polypropylene coating. Compared with the process shown in Scheme 1, in this method the amine-containing material (in Scheme 2, labeled APP) was prepared prior to coating the polypropylene slide. Substitution of chlorine in CPP with polyethyleneimine gave the aminated polypropylene (APP) in solution. The PP slide was then coated with the APP solution, and the slide was washed with deionized (D.I) water and acetone to completely remove unreacted PEI and PEI salt. The coated APP/PP slide was quaternized with alkyl halide to give the quaternized amine coated product (QPP/PP).

Scheme 2: First modified process for the preparation of antimicrobial polypropylene

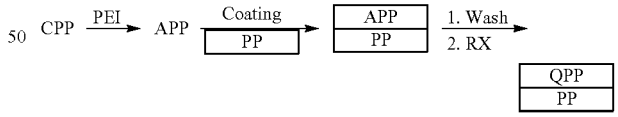

Specific experimental procedures for one sample prepared according to the modified process are as follows. Polyethyleneimine (PEI, branched, Mw=25,000; 10,000 by GPC, 0.33 g) was dissolved in acetone (15 ml), and added to 10 ml of Chlorinated polypropylene solution (5 wt % in toluene). The mixture was stirred at 50° C. for 3 days. Deposited polymer was found during the reaction. After the reaction, the solution was carefully removed from the deposited polymer. The PP slide (1 cm×1 cm) was dipped into this solution. The resulting APP coated PP slide was washed with D.I water and acetone to completely remove unreacted PEI and PEI salt. After drying under vacuum, the slide was put into a vial followed by adding acetonitrile (2 ml) and methyl iodide (0.2 ml). The mixture was stirred at 50° C. overnight. The resulting PP slide (QPP/PP) was washed with D.I water and acetone, and dried under vacuum.

Example 3

Description for the second modified coating process. Scheme 3 shows the method for antimicrobial polypropylene coating. This method prepares a quaternized amine compound (quaternized polyethyleneimine in Scheme 3, labeled QPEI) prior to coating a substrate (polypropylene in Scheme 3, labeled PP). In Scheme 3, polyethyleneimine (labeled PEI) is the base amine material for preparing a quaternized amine compound. After obtaining quaternized amine as solid, it is dissolved in a suitable solvent and coated to polypropylene surface.

Scheme 3: The QPEI coating process

Specific experimental procedures for one sample prepared according to the QPEI process are as follows. To polyethyleneimine (PEI, branched, Mw=25,000, 0.96 g) in t-Amyl alcohol (12 mL) was added 1-Bromohexane (11.6 ml) followed by K2CO3 (3.6 g). The bottle was sealed and stirred for 24 hrs at 95° C. After removing solids by filtration, methyl iodide (2.7 ml) was added to the solution. The mixture was stirred in a sealed bottle for another 24 hrs at 60° C. The product solution was passed through a cotton plug to remove solid precipitates, and the resulting solution was put in a vacuum evaporator to reduce the volume of solvent to about 10 ml. Hexane was added to the solution to precipitate the product. The product-hexane mixture was stirred overnight at room temperature, the product was collected by filtration, washed with hexane, and dried under vacuum. The yield of product, quaternized polyethyleneimine (QPEI) was 3.37 g (beige fine powder).

The resulting QPEI was dissolved in methanol to make 5 wt % or 10 wt % solution. A PP slide (1 cm×1 cm) was dipped into the QPEI-methanol solution. After 5 min, the coated PP slide was taken out from the solution and dried under vacuum.

The amount of quaternized amine was characterized according to the procedure described in Huang et al., "Antibacterial Polypropylene via Surface-Initiated Atom Transfer Radical Polymerization," *Biomacromolecules* 2007, 8, 1396-1399. Results are provided in Table 2 for four samples prepared according to two different methods as described above.

TABLE 2

Density of quaternized amine in Coated Polypropylene

| Sample # | Method | PEI (Mw) | OPP (ug) |
|---|---|---|---|
| A | QPEI coating (10 wt %) | 25,000 | 4.9 |
| C | QPEI coating (5 wt %) | 25,000 | 3.4 |
| L | The modified coating | 25,000 | 13.6 |
| N | The original coating | 25,000 | 8.9 |

Example 4

Antibacterial Screening Study

Samples were tested to determine if the prepared quaternary ammonium polypropylene coated polypropylene (QPP/PP) material has inhibitory or cidal activity against bacteria and to determine if it has residual action after the initial bacterial exposure.

Study Design: Squares of quaternary ammonium polypropylene on polypropylene (QPP/PP) were exposed to suspensions of *Pseudomonas aeruginosa* and *Staphylococcus aureus* to determine if growth was inhibited and if the organisms were killed. The effect of QPP/PP on the bacteria was compared to control squares consisting of polypropylene alone, polypropylene with an overlayer of chlorinated polypropylene (CPP/PP), or polypropylene with an overlayer of aminated polypropylene (APP/PP).

Preparation of Microtiter Trays: Squares was glued to the bottom of wells in 12 well microtiter trays. Each tray had squares with different concentrations of QPP/PP as well as control squares. Each tray bottom was marked by a spot located on the upper, left hand corner, and a template indicating the contents and location of the squares in the wells was made. The trays was wrapped individually and sterilized. One tray was used with one species.

Test for Inhibition: 24 hour broth cultures of *P. aeruginosa* and *S. aureus* were prepared in tryptic soy broth. The suspensions were adjusted to concentrations of $10^5$ orgs/ml. One ml of broth was added to each well in a tray. The tray was incubated for 18 hours at 35° C. The wells were examined for turbidity as indicating growth. Growth indicated lack of inhibitory activity.

Test for Cidal Activity: Every well was subcultured to a blood agar plate, and the plates were incubated for 18-24 hours at 35° C. Colonies were counted. Growth indicated a lack of cidal action.

Test for Residual Activity: Immediately after the plates were subcultured and all broth had been removed from each well, sterile tryptic soy broth was added to the wells, and the well was incubated again at 18 hours at 35° C. The wells were examined for growth. Growth indicated lack of residual antibacterial activity.

Specific procedures followed the following four-day schedule.

Day 1: cultures of *S. Aureus* and *P. Aeruginosas* were prepared.

Day 2: five sample trays were prepared—two containing sample A, two containing sample C, and a fifth containing a polypropylene control. An aliquot of solution containing cultured *S. Aureus* was placed in a tray containing sample A and in a tray containing sample C. An aliquot of solution containing cultured *P. Aeruginosas* was placed in a tray containing sample A and in a tray containing sample C.

Day 3: aliquots (0.5 ml) from each of the four sample trays were removed and placed in cultures.

Day 4: the number of colonies in each culture was counted.

Figure 1B:
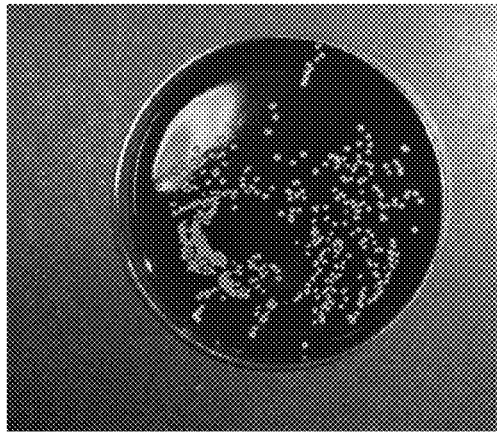
Figure 1C:
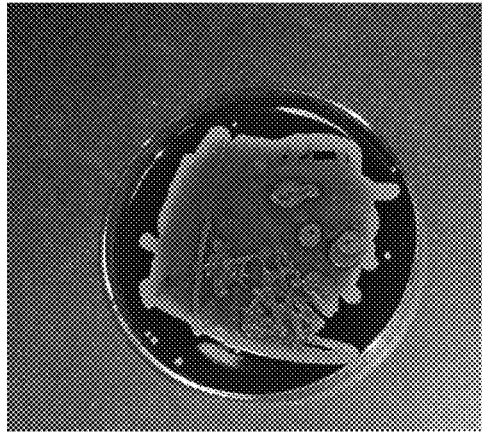

Samples A and C were subjected to in vitro growth tests as described in the preceding paragraphs. Results of the experiment are provided in FIGS. 1 and 2 and Table 3. The *S. Aureus* culture grown from solution contacting a polypropylene control (i.e., a sample material containing no anti-microbial coating material) is shown in FIG. 1c; full bacterial growth (>200 colonies) is observed. The culture of *S. Aureus* grown from a solution contacting sample A is shown in FIG. 1a; no bacteria colonies are present. The culture of *S. Aureus* grown from a solution contacting sample C is shown in FIG. 1b; more than 200 bacteria colonies are present, but significantly fewer colonies are present compared with the control sample. These results show that the coatings present on samples A and C inhibited the growth of *S. Aureus*, a Gram + bacteria.

The *P. Aeruginosas* culture grown from solution contacting a polypropylene control (i.e., a sample material containing no anti-microbial coating material) is shown in FIG. 2c; full bacterial growth (>200 colonies) is observed. The culture of *P. Aeruginosas* grown from a solution contacting sample A is shown in FIG. 2a; bacterial growth is observed, but significantly less compared with the control. The culture of *P. Aeruginosas* grown from a solution contacting sample C is shown in FIG. 1b; more than 200 bacteria colonies are present, but significantly fewer colonies are present compared with the control sample. These results show that the coatings present on samples A and C inhibited the growth of *P. Aeruginosas*, a Gram – bacteria.

TABLE 3

Results of Biological Screening for Coated Polypropylene

| Sample # | Method | PEI (Mw) | Coating Sol'n | Result (# colony)[a] |
|---|---|---|---|---|
| A | QPEI coating | 25,000 | 100 mg QPEI/1 mL MeOH | S. (~0), P. (<50) |
| C | QPEI coating | 25,000 | 50 mg QPEI/1 mL MeOH | S. (<200), P. (<200) |

[a]S: *Staphylococcus aureus*, P: *Pesudomonas aeruginosa*

Example 5

Contact Lens Studies

Preparation of Bacteria and Contact Lenses. *P. aeruginosa*, isolated from a CLARE (Contact Lens-induced Acute Red Eye) event in humans, is grown overnight in tryptone soya broth (TSB), washed in phosphate-buffered saline (PBS; NaCl 8 g L-1, KCl 0.2 g L-1, Na2HPO4 1.15 g L-1, and KH2PO4 0.2 g L-1) and re-suspended in PBS to an OD660 nm of 2.9. The suspension is examined by light microscopy to ensure clumping does not occur. Sterile contact lenses are removed from vials and washed three times in 1 mL PBS before use and then immersed in 1 mL of bacterial suspension for approximately 30 minutes before insertion.

The contact lenses are removed from the bacterial suspension with sterile forceps, washed once in 1 mL sterile PBS, and placed on the eyes. The lenses are evaluated for the number of both total and viable adherent bacteria before insertion and on removal at the completion of the experiment. The viable bacteria are quantitated by homogenizing the lenses (e.g., using a DIAX 500 homogenizer; Heidolph, Berladingen, Germany). A 100-µL aliquot of the resulting homogenate is serially diluted 1:10 in sterile PBS. Triplicate aliquots (20 µL) of each dilution, including the original homogenate, are plated onto nutrient agar. The plates are incubated for 24 hours at 37° C. before colony-forming units (cfu) are enumerated and the units per lens calculated. The total number of bacteria on the lens surface (colony-forming units per square millimeter) is estimated by using light microscopy.

Preparation of bacteria and contact lenses for *S. aureus*, a strain isolated from a case of CLPU (Contact Lens-induced Peripheral Ulcers) proceeds similarly as described above. The bacteria are grown overnight in TSB and then washed three times in PBS. The bacteria are re-suspended in PBS to an OD660 nm of 2.0. The suspension is examined by light microscopy to ensure the excessive clumping does not occur. Contact lenses are washed three times in 1 mL PBS before use and immersed in 1 mL of the bacterial suspension for approximately 30 minutes before insertion into the eyes (e.g., rabbit eyes).

What is claimed is:

1. A coating layer on a surface of a substrate comprising: a polymeric material comprising polypropylene having quaternary amine groups covalently attached to the polypropylene; wherein the polymeric material is non-covalently attached to the substrate surface.

2. The coating layer of claim 1, wherein the quaternary amine groups are covalently attached to sidechains of the polypropylene, or wherein the quaternary amine groups are incorporated into the backbone of the polymeric material.

3. An anti-microbial coated substrate comprising a substrate and a coating disposed on a surface of the substrate, wherein the coating comprises a polymer comprising polypropylene that is non-covalently attached to the substrate, and wherein the polypropylene comprises a plurality of quaternary amine groups.

4. The material of claim 3, wherein the substrate is a polymeric material, and wherein the coating is bonded to the substrate via hydrogen bonding, Van der Waals forces, ionic bonding or a combination thereof.

5. The material of claim 3, wherein the polymer is water-insoluble, and further wherein the polymer is not a polyamino acid.

6. The anti-microbial coated substrate of claim 3, wherein the plurality of quaternary amine groups comprise polymer backbone groups.

7. The material of claim 3, wherein the coating is prepared by a method comprising reacting a first polymer comprising polypropylene having chloro, bromo, or iodo functional groups and a second polymer comprising second functional groups, wherein the chloro, bromo, or iodo functional groups and the second functional groups are capable of reacting to form secondary, tertiary, or quaternary amines.

8. The anti-microbial coated substrate of claim 7, wherein the polypropylene is a chlorinated polypropylene.

9. The anti-microbial coated substrate of claim 8, wherein the chlorinated polypropylene has a molecular weight in the range of 1000 Daltons to 1,000,000 Daltons.

10. The anti-microbial coated substrate of claim 7, wherein the second polymer is a polymeric or oligomeric polyalkyleneimine.

11. The anti-microbial coated substrate of claim 9, wherein the second polymer is a poly(ethyleneimine).

12. The anti-microbial coated substrate of claim 11, wherein the poly(ethyleneimine) is a linear poly(ethyleneimine) comprising secondary amines.

13. The anti-microbial coated substrate of claim 11, wherein the poly(ethyleneimine) is a branched poly(ethyleneimine) comprising primary, secondary, and tertiary amines.

14. The anti-microbial coated substrate of claim 11, wherein the poly(ethyleneimine) has a molecular weight in the range of 350 Daltons to 1,000,000 Daltons.

* * * * *